United States Patent
Rowley (10) Patent No.: US 12,054,354 B2
(45) Date of Patent: Aug. 6, 2024

(54) MOTORIZED REEL APPARATUS FOR NEEDLE BIOPSY OPERATIONS

(71) Applicant: Justin Rowley, Edmond, OK (US)

(72) Inventor: Justin Rowley, Edmond, OK (US)

( * ) Notice: Subject to any disclaimer, the term of this patent is extended or adjusted under 35 U.S.C. 154(b) by 190 days.

(21) Appl. No.: 17/713,924

(22) Filed: Apr. 5, 2022

(65) Prior Publication Data

US 2022/0315377 A1 Oct. 6, 2022

Related U.S. Application Data

(63) Continuation-in-part of application No. 29/783,078, filed on May 11, 2021.

(Continued)

(51) Int. Cl.
*B65H 75/44* (2006.01)
*B65H 75/26* (2006.01)

(52) U.S. Cl.
CPC ....... *B65H 75/4486* (2013.01); *B65H 75/265* (2013.01); *B65H 75/4413* (2013.01);
(Continued)

(58) Field of Classification Search
CPC .... B65H 75/34; B65H 75/38; B65H 75/4402; B65H 75/4405; B65H 75/4407; B65H 75/4413; B65H 75/4415; B65H 75/4471; B65H 75/4481; B65H 75/4484; B65H 75/4486; B65H 75/4457; B65H 75/446; B65H 75/4428; B65H 75/00; B65H 75/10; B65H 75/36; B65H 75/362; B65H 75/364; B65H 75/26; B65H 75/265; B65H 75/30;
(Continued)

(56) References Cited

U.S. PATENT DOCUMENTS

| 1,659,160 A | * | 2/1928 | Richards | ................. F21V 27/00 |
| | | | | 191/12.2 R |
| 2,702,674 A | * | 2/1955 | Willson | ................... B67D 7/40 |
| | | | | 137/355.23 |

(Continued)

FOREIGN PATENT DOCUMENTS

| CN | 109607327 A | * | 4/2019 | ......... B65H 75/4481 |
| FR | 3083534 A1 | * | 1/2020 | ......... B65H 75/4415 |
| WO | WO-2020238545 A1 | * | 12/2020 | ............. B65H 54/52 |

OTHER PUBLICATIONS

Bronchoscope, https://medical.olympusamerica.com/products/bf-uc180f-ebus-bronchoscope.

*Primary Examiner* — Michael R Mansen
*Assistant Examiner* — Raveen J Dias (57) ABSTRACT

A motorized reel apparatus suitable for endobronchial ultrasound bronchoscopy (EBUS) is presented. The present invention attaches to any suitable corresponding biopsy needle stylus. The motorized reel apparatus contains a reel housing, a spool drum, a spool spindle, a motor, and a controller. The reel housing contains wire outlet aperture. The wire outlet aperture traverses through the reel housing. The spool drum is connected within the reel housing. The spool spindle operatively engages along the spool drum, where the spool spindle can dispense a biopsy wire along the wire outlet aperture. The motor is rotatably engaged to the spool spindle. The controller is electrically connected to the motor, where the controller is configured to retract or deploy a biopsy wire along the wire outlet aperture.

13 Claims, 7 Drawing Sheets

Related U.S. Application Data (60) Provisional application No. 63/170,693, filed on Apr. 5, 2021.

(52) U.S. Cl.
CPC ..... *B65H 75/4415* (2013.01); *B65H 75/4428* (2013.01); *B65H 75/4471* (2013.01); *B65H 75/4484* (2013.01); *B65H 75/4407* (2013.01); *B65H 2403/40* (2013.01)

(58) Field of Classification Search
CPC ............ B65H 2701/33; B65H 2701/34; B65H 2701/36; A61B 1/005; A61B 1/0051; A61B 1/0016; A61B 8/12
See application file for complete search history.

(56) References Cited

U.S. PATENT DOCUMENTS

| | | | | |
|---|---|---|---|---|
| 3,232,555 A * | 2/1966 | Gorrell | ............... | B65H 75/4407 242/390.8 |
| 3,539,123 A * | 11/1970 | Shutt | ................. | B65H 75/4449 242/390.8 |
| 3,563,481 A * | 2/1971 | Stahmer | ................. | B65H 75/38 242/397.3 |
| 4,832,074 A * | 5/1989 | Li | .......................... | A62C 33/00 137/355.2 |
| 4,842,108 A * | 6/1989 | Anderson | ............... | H02G 11/02 242/390.8 |
| 4,945,938 A * | 8/1990 | Ponsford | ................. | B60P 3/035 137/15.01 |
| 5,099,911 A * | 3/1992 | Vowles | .............. | B65H 75/4413 165/95 |
| 5,211,203 A * | 5/1993 | Vollweiler | ......... | B65H 75/4402 137/355.21 |
| 5,265,671 A * | 11/1993 | Vowles | .............. | B65H 75/4413 165/95 |
| 5,887,815 A * | 3/1999 | Pierce | ................ | B65H 54/2896 242/909 |
| 6,063,035 A * | 5/2000 | Sakamoto | .............. | A61B 8/445 600/462 |
| 6,273,225 B1 * | 8/2001 | Park | ....................... | B65H 75/40 191/12.4 |
| 6,371,907 B1 * | 4/2002 | Hasegawa | .............. | A61B 1/009 600/152 |
| 8,061,644 B1 * | 11/2011 | Dion | .................. | B65H 75/4405 242/157.1 |
| 8,095,223 B2 * | 1/2012 | Cleary | ............... | A61M 25/0113 607/115 |
| 8,651,412 B2 | 2/2014 | Hernik | | |
| 9,062,921 B2 * | 6/2015 | Gromes, Sr. | .......... | F28G 15/003 |
| 9,480,781 B2 | 11/2016 | Kang et al. | | |
| 9,908,754 B2 * | 3/2018 | Hall | ........................ | B66D 1/12 |
| 10,336,590 B2 * | 7/2019 | Hall | ........................ | B66D 1/38 |
| 2002/0032365 A1 * | 3/2002 | Hasegawa | ............ | A61B 1/0669 600/102 |
| 2004/0054259 A1 * | 3/2004 | Hasegawa | ............ | A61B 1/0052 600/152 |
| 2005/0051406 A1 * | 3/2005 | Hopper | ................ | B65H 75/486 248/330.1 |
| 2009/0277988 A1 * | 11/2009 | Hernik | ............... | B65H 75/4481 242/478.2 |
| 2010/0294872 A1 * | 11/2010 | Wang | ................ | B65H 75/4486 242/390.8 |
| 2012/0025002 A1 * | 2/2012 | Zink | ................ | B65H 75/4402 242/390.2 |
| 2012/0227815 A1 * | 9/2012 | Zink | ................ | B65H 75/4415 137/355.2 |
| 2012/0247579 A1 * | 10/2012 | Park | .................... | B65H 75/4478 137/355.26 |
| 2014/0277097 A1 | 9/2014 | Castleberry et al. | | |
| 2018/0251352 A1 * | 9/2018 | Ijadi-Maghsoodi | ..... | B66D 1/28 |
| 2019/0039856 A1 * | 2/2019 | Summer | ............... | B65H 75/425 |
| 2019/0300325 A1 * | 10/2019 | Mackie | .................. | B65H 61/00 |
| 2019/0322481 A1 * | 10/2019 | Dion | .................. | B65H 75/4489 |
| 2020/0095089 A1 * | 3/2020 | Zahnd | ................ | B65H 75/4484 |
| 2023/0173561 A1 * | 6/2023 | Grode | ................ | B65H 75/4486 15/104.33 |

\* cited by examiner

MOTORIZED REEL APPARATUS FOR NEEDLE BIOPSY OPERATIONS

FIELD OF THE INVENTION

The present invention relates to wire dispensing units. More specifically, the present invention relates to wire dispensing units for needle biopsy's.

BACKGROUND OF THE INVENTION

Endobronchial ultrasound bronchoscopy (EBUS) is a procedure that is used to diagnose different types of lung disorders which result in mediastinal lymphadenopathy, including inflammation, infections or cancer. Pulmonologists use a special bronchoscope with an ultrasound probe attached to the distal end, in conjunction with the standard camera and working channel. This bronchoscope is inserted into the airway of patients to create local images of their lungs and nearby lymph nodes in order to accurately locate and evaluate areas seen on chest x-rays or body scans. Once the lymph nodes are thoroughly mapped out, a needle is passed down the working channel of the bronchoscope. The Pulmonologists and a technician, using a specially designed needled, visualize the needle biopsy of the chosen lymph node under ultrasound. The needle is then removed from the bronchoscope for removal of the acquired specimen.

EBUS has proven to be an effective, less invasive than prior methods, procedure for patients requiring a variety of diagnoses. Whether linear or radial EBUS, the technological advances delivered through the EBUS bronchoscope and biopsy needles provide patients with efficient results and faster recovery times. The device at hand seeks to improve, particularly, the biopsy needle and the function of the inner stylet wire. One of the major downfalls of EBUS procedures, is the time spent handling the inner stylet wire. Once the needle is inserted into the desired lymph node, the inner guide wire must be completely removed from the needle apparatus, allowing space for the cellular matter to collect within the coring needle, and to add suction to the biopsy collection via a suction syringe attached to the top of the needle body/handle. After the biopsy needle is removed, the specimen is removed from the biopsy needle using sterile solution and compressed air. The inner stylet wire must then be completely reinserted into the needle apparatus before the next pass can begin. This process is cumbersome and time consuming for the physician and technician, with needle and biopsy handling comprising a large majority of the EBUS procedure time. The continued handling of the inner stylet wire throughout the case also lends to multiple opportunities for wire mishaps. Dropping the wire or splashing of biological material off of the wire during handling, are always of concern for the involved clinicians.

This device seeks to automate the stylet wire process of EBUS using an externally encased, threaded wire reel component, powered by a small, battery powered D/C motor that will spin the wire reel and spool/unspool the wire. Eliminating the need for the physician or assisting technician to physically handle the wire throughout the case.

SUMMARY OF THE INVENTION

The present invention is a motorized reel apparatus suitable for endobronchial ultrasound bronchoscopy (EBUS). The present invention attaches to any suitable corresponding biopsy needle stylus. The motorized reel apparatus comprises a reel housing, a spool drum, a spool spindle, an adjustment element, a drive shaft, a motor, and a controller. The reel housing comprises a wire outlet guide and a wire outlet aperture. The spool drum comprises a spindle receiving channel, wire receiving groove, and a wire inlet. The spool spindle comprises a spindle body and a wire shuttle. The spool drum is connected within the reel housing. The spindle body is connected terminally adjacent to the wire shuttle. The spindle receiving channel traverses into the spool drum. The wire receiving groove traverses into the spool drum. The spindle body is operatively engaged to the spindle receiving channel through the adjustment element, where the spindle body is configured to rotate and traverse along the spool drum, and where the adjustment element is configured to adjust the spool spindle along the spool drum in length. The wire shuttle is operatively engaged to the wire receiving groove. The wire inlet traverses through the spool drum. The wire outlet aperture traverses through the housing. The wire guide is connected between the wire inlet and the wire outlet aperture. The wire shuttle, the wire inlet, and the wire guide are in fluid communication to each other. The drive shaft is rotatably connected within the reel housing. The drive shaft is torsionally engaged to the spool spindle. The drive shaft is slidably connected to the spool spindle. The drive shaft is rotatably engaged to the motor. The controller is electrically connected to the motor.

This device uses a 0.015 mm flexible, metal inner stylet wire that is attached to a threaded wire reel component. When in the ready for use position, this threaded reel is housed inside a corresponding reverse threaded housing component. This housing component is formed into the structure of the body of the device. The body or the device has various design features aimed at providing a simple, safe and drastically more efficient needle biopsy process. These external features include ergonomic up and down control buttons which operate the directional current of power to the D/C motor. The D/C motor has a small gear attached to the shaft of the motor. This small gear from the motor then contacts another small gear, which is attached to the side frame/body of the external case. This gear is merely intended to step down the RPM ratio of the D/C motor/gear. This "middle" gear, then finally contacts below with another small gear, which is attached to a square shaft that runs through the center of the gear. This square shaft protrudes into the body of the device and is the guide and power source for the stylet wire reel to spin in and out on the threads. The continuous square shaft becomes circular again distal of the gear, or closer to the external device body wall, so that it may go through a small opening in the side body of the external body wall. This makes the circular portion of the continuous shaft protrude slightly through the external body wall, so that a circular hold/cap piece may be compressed or screwed onto the end of the shaft. Because this shaft protrudes through the external body wall, it holds the shaft in a centered position on the right end of the shaft, when the other end terminates inside of the stylet wire reel component's slightly larger square opening that runs through the middle. The circular hold/cap piece is intended to hold/lock the shaft to the device external body wall and has a formed or printed line across the middle of the upper face of the cap. When the D/C motor powers the gears, subsequently the shaft, this spins the circular cap on outside of the external body wall so that the indicated printed or formed line can be used as a visual aid that the motor is spinning, and the wire reel is in fact in motion. A clear thin plastic cover will go over this spinning cap cover area that will be formed into the body of the external device body wall to create a viewing window of the spinning component but prevents the users from incidentally contacting or obstructing the spinning component.

The wire reel component is comprised of one formed piece of material, which has 3 major components. The first being the thread components, which are designed to travel down the corresponding opposite threads of a circular channel which is framed out by a square structure integrated into the body of the device. The next being the smooth, slightly less wide wire reel section which received/contains the wire shuttle component. This area is circular and smooth. The last main component being a hollow, square shaft like opening that runs the length of the wire reel body from end to end through the middle. The shaft like opening is very slightly wider than the corresponding shaft from the shaft that contains the gear that receives power from the D/C motor. The shaft that directly receives power from the D/C motor is slightly narrower than opening in the middle of the wire reel body. This shaft is connected and stabilized, similar to the middle gear, in that the shaft protrudes through the side of the external body case/housing through a small opening. When assembling, the wire reel body would initially be threaded into the corresponding circular threads, contained within the formed threaded body components of the device. This would center the wire reel body within the center of the formed structural threaded body component. The square opening or channel that runs through the middle of the wire reel body, would then be visualized as open. The separate shaft that contains the gear, which receives the power from the D/C motor, is then slid into the slightly larger corresponding shaft/opening that runs through the duration of the middle of the wire reel body. The shaft that contains the gear, is only slightly narrower than the corresponding shaft, allowing the two components to slide over each other without generating friction. This gear shaft is long enough to slide into the body of the wire reel approximately ¾ of the total length of the body of the wire reel. Therefore, when the D/C motor puts power to the gears, it turns the geared shaft, which due to the explained design, turns the shaft which causes the wire reel body to turn and begin to spin down the threads, towards to opposite side of the device body.

As the wire reel body spins down the threads, the wire is subsequently coiled into the wire receiving groove on the inside of the spool drum. The external up and down buttons on the outside body of the device, will control the power current to the D/C motor. With the wire in the fully extended from the reel out of the body of the device into the needle so that the tip of the wire is at the tip of the needle, the up button is pushed which puts power to the shaft and causes the wire reel body to spin clockwise down the duration of the threads, to travel a predetermined total distance of 1000 mm for the wire to travel, up or down. 960 mm is the total length of the wire from the top of the needle handle where the wire enters the needle handle body, to the tip of the needle. Another 40 mm of travel is needed to cover the added distance of a 3-way stop cock, so that wire can be reeled up through the 3-way stop-cock and into the lower external body protrusion. Once the up button has been depressed until the wire has fully retracted into the wire receiving groove in the body of the device, the face of the threaded wire reel component will then contact a PCB sensor located at the distal end of the threaded body component. This contact sensor will indicate to the control PCB to stop power to the D/C motor, therefore, stopping the spin of the wire reel body. When this contact sensor is depressed, the D/C current will be stopped to the motor, but a blue LED indicator light will be lit to indicate that the wire is fully withdrawn into the body of the device into the wire receiving groove. This blue LED light is intended to be on the control PCB, located near the top section of the body of the device. The design of the external body allows for a transparent, clear ring to circumvent the external body of the device near the top. When this blue LED is lit, this LED light will glow through the corresponding clear ring built within the external body of the device. This will indicate to the users that the wire is fully reeled into the housing of the device, and the user can now apply suction to the three way stop cock, if applicable, and acquire the desired specimen. Once the clinicians are ready for the next pass, the down button on the external body will be depressed.

This will allow for the D/C motor to apply power to the gear shaft reel to turn the shaft counterclockwise, therefore, spinning the threaded wire reel body back out of the threaded body component and towards the beginning neutral position. When the wire reel body spins counterclockwise back to the beginning position, the wire is then back to the fully extended position with the tip of the wire being at the desired position for needle biopsy near the end of the needle. Once the wire reel body reaches the beginning, neutral extended position, another contact sensor is depressed by the end wall of the wire reel body. This stops the supply of power to the D/C motor to stop the turn of the wire reel body. When this contact sensor is depressed, a green LED light located on the control PCB near the top section of the body of the device, is lit to glow the aforementioned clear ring green in the body of the device to indicate to the clinicians that the wire reel has stopped turning and the wire is in the fully extended, ready to needle biopsy position. Anytime neither of these two sensors are depressed, it indicates to the PCB that both of the contact sensors are open. When they are both open, a red LED light located on the control PCB near the upper body of the device, will glow the aforementioned clear ring red to indicate to the clinicians that the wire is somewhere in the needle channel and is not ready for proper needle biopsy or specimen retrieval.

The D/C motor and PCB components will be powered by two circular CR1632 3V type lithium batteries. These thin, circular batteries will be located near the upper portion of the main device body, above the D/C motor and housing components, which are formed into the device threaded body component on the top side. The batteries will be activated out of the packaging by removing a plastic contact preventer located between the two batteries, that is installed during manufacturing. The plastic tab will protrude through a small slit opening positioned parallel to the contact points of the batteries. Once this tab is externally pulled and the batteries can contact each other, the device will be ready for use. The control sensors for the up down external buttons are push on, release off contact switches. The two up/down buttons are built into and secured to the frame of the device body housing. The subsequent device wiring is routed along the inside walls of the device, to ensure free movement of the D/C motor shaft, gears, and the threaded wire reel shaft, which are located near the center/core of the device. The 0.015 mm flexible stylet wire is guided off of the reel down a formed chute, towards and out of the bottom opening of the device. The chute tapers to guide the stylet wire from the reel into a narrower opening, which is in-line with the male threaded connection adapter on the distal end of the device, which connects to the 3-way stop-cock. There is a small flexible rubber or plastic diaphragm, towards the bottom or distal end of this chute, in which the stylet wire travels through a small opening in the middle of the diaphragm, with only enough friction to clean/wick and stabilize the wire as it travels through it up and down.

This is to prevent any biological material that may accumulate on the stylet wire during the process of needle biopsy, from being withdrawn up into the device, therefore, keeping the wire reel and internal components clean during operation. This chute off the bottom of the device, is formed and contained within the external device body protrusion. This external protrusion floats over a slightly smaller connection component, that allows the whole device body to move up and down over this small component. This small connection component has a male leur-lock threaded connection formed on the distal end, with the intent to connect to the female connection of a leur-lock 3-way stop-cock. The point of the 3-way stop-cock is to allow for rotational spinning of the wire reel device once attached to the top of the needle handle. The wire reel device body can be positioned so the up/down buttons are in the best 360-degree orientation for easy use of operation. Once the desired position is chosen, the 3-way stop-cock is tightened, and the wire reel device body is now locked into the correct orientation on the needle body handle. Also, the perpendicular open valve of the 3 way stop-cock, which is not in-line with the wire/wire channel, is used to apply a suction syringe for specimen removal, and sterile saline and air for specimen removal post needle biopsy. This device allows the users to never have to handle the stylet wire and allows for safer retrieval and removal of needle biopsy specimens due to less dexterity and series of movements needed to retrieve and remove the specimens due to the device design.

The external lower body protrusion has an opening on one side that will be used as a view window for depth markings. These depth markings are lines on the side of the small component that slides, just slightly, on the inside of the external lower body protrusion. On the other side of the lower external body protrusion, opposite of the view window opening, is a small threaded hole opening. This threaded hole allows for a pointed-tip small screw to be screwed into the hole, through the side body of the external lower body protrusion, to make contact with the surface of the small connection component, contained just slightly narrower inside the external lower body protrusion. When the screw is hand tightened clockwise, this locks the external lower body component, therefore, the entire body of the device, into a secured position on the small sliding connection component with the male leur-lock threaded distal end. This allows for users to have the ability to slightly adjust the depth of the wire at the end of the needle tip, should it get off slightly during the case and need to be adjusted. The device body will be locked/screwed at a neutral marking on the small connection component out of the package and ready for use, with the device calibrated to have exactly 1,000 mm of total wire travel for correct position from the fully-up to fully down position. There is approximately 5 mm of adjustment that will be marked with depth line markings on the side of the small connection component. These markings can be viewed through the viewing window on the external lower body protrusion. When the screw is hand-loosened counter-clockwise, the entire device body can be adjusted 2.5 mm up or 2.5 mm down, indicated by the line markings. If the wire depth needs to be adjusted, the position can be re-secured by hand tightening the screw clockwise onto the side of the slightly smaller connection component. The device is intended to be single patient use and disposable.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

In reference to FIGS. 1-3 and 5-6, the present invention is a motorized reel apparatus 1 suitable for endobronchial ultrasound bronchoscopy (EBUS). The present invention attaches to any suitable corresponding biopsy needle stylus. The motorized reel apparatus 1 comprises a reel housing, a spool drum 12, a spool spindle 13, an adjustment element 14, a drive shaft 15, a motor, and a controller 17. In reference to FIGS. 1-6, the reel housing 11 comprises a wire outlet guide 111 and a wire outlet aperture 112. In reference to FIGS. 3-4 and 6, the spool drum 12 comprises a spindle receiving channel 121, wire receiving groove 122, and a wire inlet 123. In reference to FIGS. 3-4 and 6, the spool spindle 13 comprises a spindle body and a wire shuttle 132. The spool drum 12 is connected within the reel housing 11. The spindle body 131 is connected terminally adjacent to the wire shuttle 132. The spindle receiving channel 121 traverses into the spool drum 12. The wire receiving groove 122 traverses into the spool drum 12. The spindle body 131 is operatively engaged to the spindle receiving channel 121 through the adjustment element 14, where the spindle body 131 is configured to rotate and traverse along the spool drum 12, and where the adjustment element 14 is configured to adjust the spool spindle 13 along the spool drum 12 in length. The wire shuttle 132 is operatively engaged to the wire receiving groove 122. The wire inlet 123 traverses through the spool drum 12. The wire outlet aperture 112 traverses through the reel housing 11. The wire guide 111 is connected between the wire inlet 123 and the wire outlet aperture 112. The wire shuttle 132, the wire inlet 123, and the wire guide 111 are in fluid communication to each other. The drive shaft 15 is rotatably connected within the reel housing 11. The drive shaft 15 is torsionally engaged to the spool spindle 13. The drive shaft 15 is slidably connected to the spool spindle 13. The drive shaft 15 is rotatably engaged to the motor. The controller 17 is electrically connected to the motor. In the preferred embodiment, the reel housing 11 takes the form of any suitable enclosure, casing, or any other suitable housing implement that secures all the components the constitutes the motorized reel apparatus 1. In the preferred embodiment, the reel housing 11 is made out of any suitable material, such as, but not limited to polymer, aluminum, stainless steel, or any other suitable material. In the preferred embodiment, the reel housing 11 is scaled to any size suitable for any type of application, In the preferred embodiment, the reel housing 11 is rectangular in shape, but may take the form of any other suitable shape. In the preferred embodiment, the spool drum 12 takes the form of statically placed piece of the spooling system that is fixed within the reel housing 11. In the preferred embodiment, the spool spindle 13 takes the form of the rotary spool piece that moves along the spool drum 12. In the preferred embodiment, the adjustment element 14 takes the form of any suitable adjustment element 14 that linearly adjusts the spool spindle 13 along the spool drum 12 in length. In the preferred embodiment, the adjustment element 14 takes the form of threaded adjusters along the spool drum 12 and the spool spindle 13, where the spool spindle 13 linearly adjusts along the spool drum 12 when the spool spindle 13 is rotated. In various embodiments, the adjustment element 14 may take the form of any other suitable adjustment implement. In the preferred embodiment, the drive shaft 15 serves as the main rotary driving element that drives the spool spindle 13 when the drive shaft 15 is actuated by the motor. Additionally, the drive shaft 15 serves as a linear support guide, aligning the spool spindle 13 to the spool drum 12. In the preferred embodiment, the motor 16 takes the form of any suitable rotary driving element. In the preferred embodiment, the motor 16 takes the form of a DC motor, but may take the form of any other suitable motor, such as, but not limited to stepper motors, servo motors, or any other suitable rotary driving element. In the preferred embodiment, the controller 17 takes the form of any suitable controlling unit that allows the user to control the motor.

In the preferred embodiment, the wire outlet guide 111 serves as a wire conduit that directs the biopsy wire fed from the spool inlet to the wire outlet aperture 112. In the preferred embodiment, the spindle receiving channel 121 serves as the bored-out section of the spool drum 12 that receives the spool spindle 13. In the preferred embodiment, the wire receiving groove 122 takes the form of a coil-cut groove along the spool drum 12 that stores and winds up the biopsy wire along the spool drum 12. In the preferred embodiment, the spindle body 131 takes the form of the chassis of the spool spindle 13 that engages along the spindle receiving channel 121. In the preferred embodiment, the wire shuttle 132 serves as the primary connection body of the spool spindle 13 that mounts the biopsy wire along the spool spindle 13. In the preferred embodiment, the spool shuttle rides along the wire receiving groove 122, where the spool shuttle is configured to push or pull the biopsy wire along the wire receiving groove 122.

Figure 6:
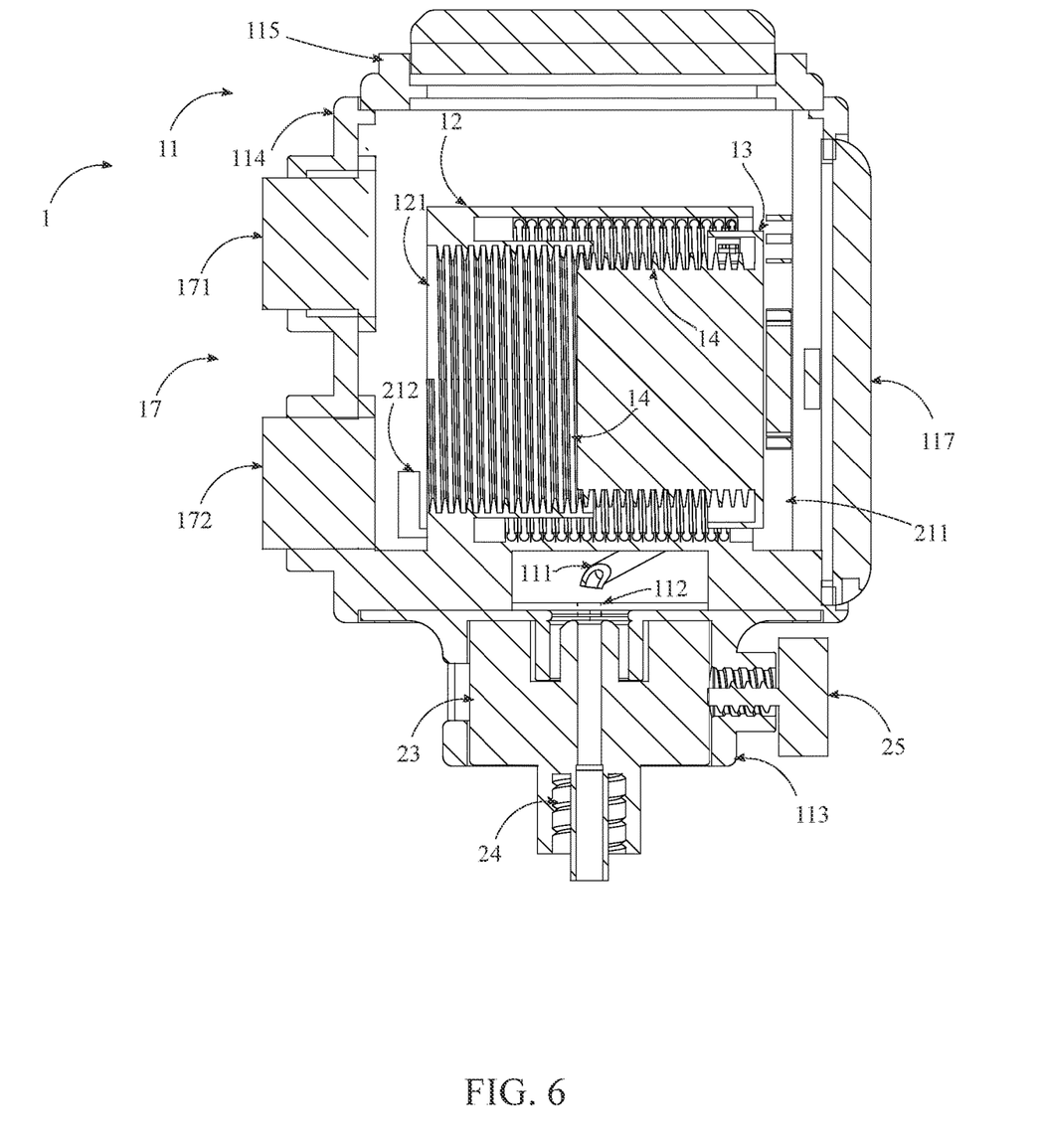
FIG. 6 is a cross sectional view taken along cutting lines B-B in FIG. 5.
Figure 7:
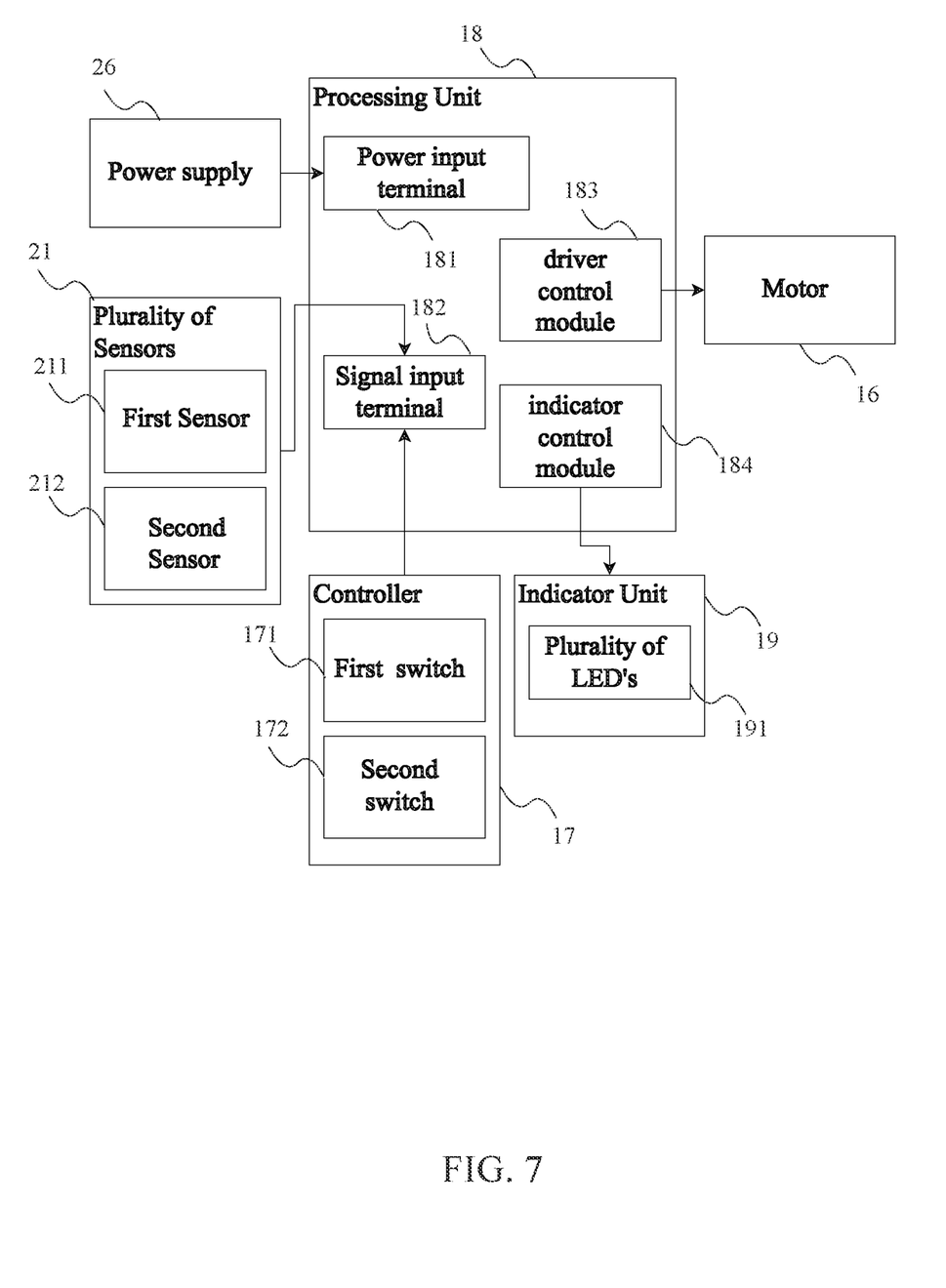
FIG. 7 is a circuit diagram used in the present invention.

In reference to FIGS. 6-7, the motorized reel apparatus 1 further comprises a processing unit, an indicator unit 19, a plurality of sensors 21, and a power supply 26. In reference to FIG. 7, the processing unit 18 comprises a power input terminal, a signal input terminal 182, a driver control module 183, and an indicator module 184. The power supply 26 is electrically connected to the power input terminal 181. The plurality of sensors 21 is electronically connected to the signal input terminal 182. The controller 17 is electronically connected to the signal input terminal 182. The motor 16 is electronically connected to the driver control module 183. The indicator unit 19 is electronically connected to the indicator control module. In reference to FIGS. 6-7, the plurality of sensors 21 comprises a first sensor 211 and a second sensor 212. The first sensor 211 is connected adjacent to the spool drum 12. The second sensor 212 is connected adjacent to the spool drum 12, longitudinally opposite from the first sensor 211. The first sensor 211 and the second sensor 212 are electronically connected to the signal input terminal 182. In the preferred embodiment, the first sensor 211 and the second sensor 212 are contact sensors. In the preferred embodiment, the processing unit 18 handles and executes all general electrical and electronic functions of the motorized reel apparatus 1. In the preferred embodiment, the power input terminal 181 serves as a voltage regulating input plug for the electrically connected power supply 26. In the preferred embodiment, the power supply 26 takes the form of any suitable power supply 26, such as, but not limited to disposable batteries, rechargeable batteries, direct power feed, or any other suitable power supply 26. In the preferred embodiment, the signal input terminal 182 serves as the main signal terminal for handling signal feedback from the controller 17 and the plurality of sensors 21. In the preferred embodiment, the driver control module 183 serves as the motor control port. In the preferred embodiment, the indicator module 184 serves as the indicator control port for the indicator unit 19. In the preferred embodiment, the indicator unit 19 takes the form of a visual wire displacement indicator but may take the form of any other suitable indicator unit 19 that aids the user in visualizing biopsy wire displacement along the motorized reel apparatus 1. In the preferred embodiment, the first sensor 211 and the second sensor 212s serves as spool spindle 13 end stop switches that disables the motor 16 when the spool spindle 13 contacts the first sensor 211 or the second sensor 212.

In reference to FIG. 7, the indicator unit 19 comprises a plurality of LED's. The plurality of LED's 191 is distributed within the reel housing 11. The plurality of LED's 191 is electronically connected to the indicator control module. In reference to FIGS. 1, 5, and 6-7, the controller 17 comprises a first switch and a second switch 172. The controller 17 is connected adjacent to the reel housing 11. The first switch 171 and the second switch 172 are distributed about the reel housing 11. The first switch 171 and the second switch 172 are electronically connected to the signal input terminal 182. In the preferred embodiment, the plurality of LED's 191 serves as a multi-colored visual indicator, where the colored lights emitted by the plurality of LED's 191 permeates and diffuses through the reel housing 11. Working in conjunction with the first sensor 211 and the second sensor 212, the plurality of LED's 191 denotes different colors that indicate the positioning of the biopsy wire along the spool spindle 13 and the spool drum 12. Additionally, the illuminated feature denotes that the motorized reel apparatus 1 is turned on. In the preferred embodiment, the first switch 171 and the second switch 172 take the form of momentary switched buttons that serves as the primary controlling elements for the controller 17. More specifically, the first switch 171 actuates the motor 16 to spin in one direction, while the second switch 172 actuates the motor 16 to spin in the opposite direction. This control function will retract or deploy the biopsy wire along the wire outlet aperture 112.

Figure 1:
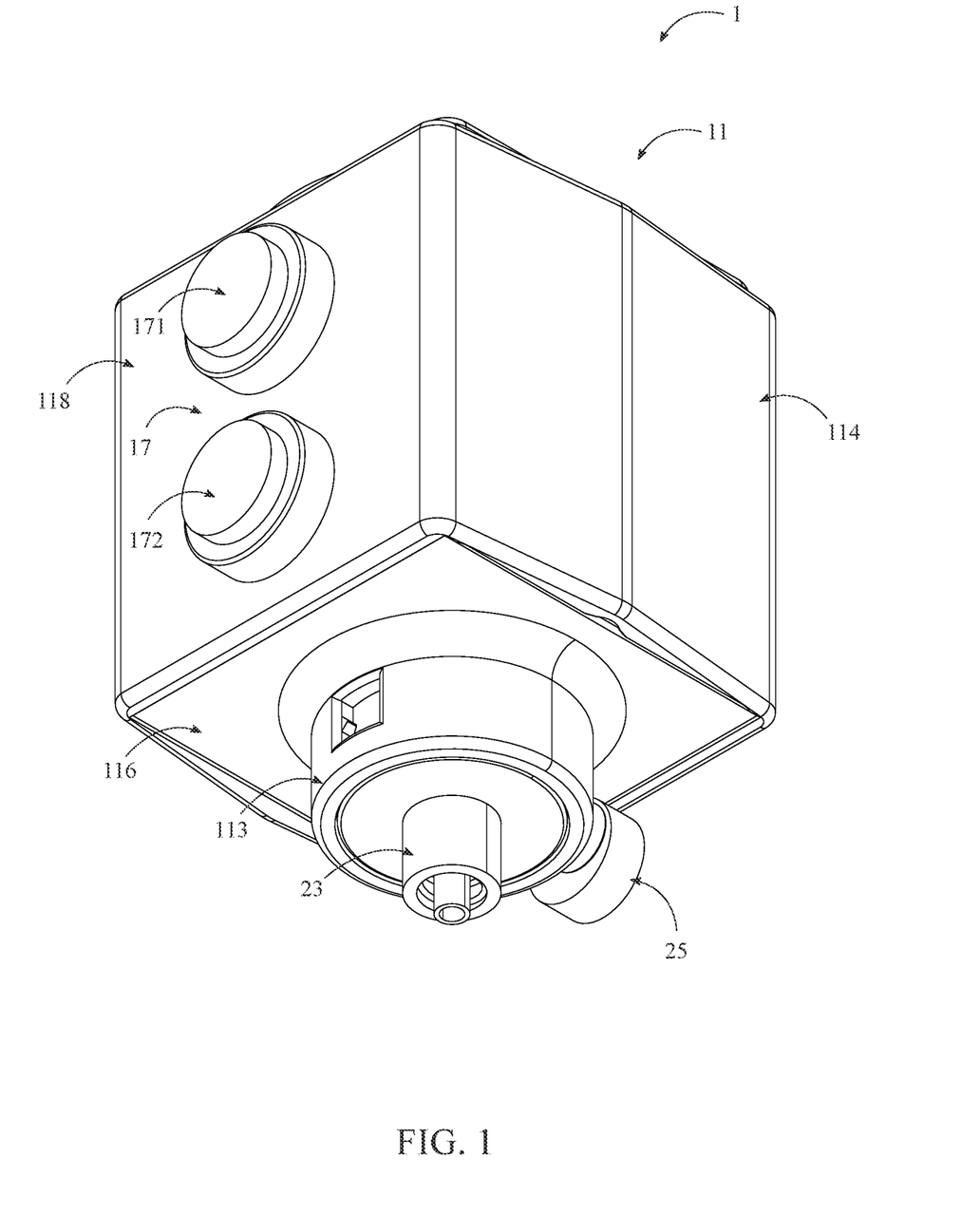
FIG. 1 is a bottom perspective view of the present invention.
Figure 2:
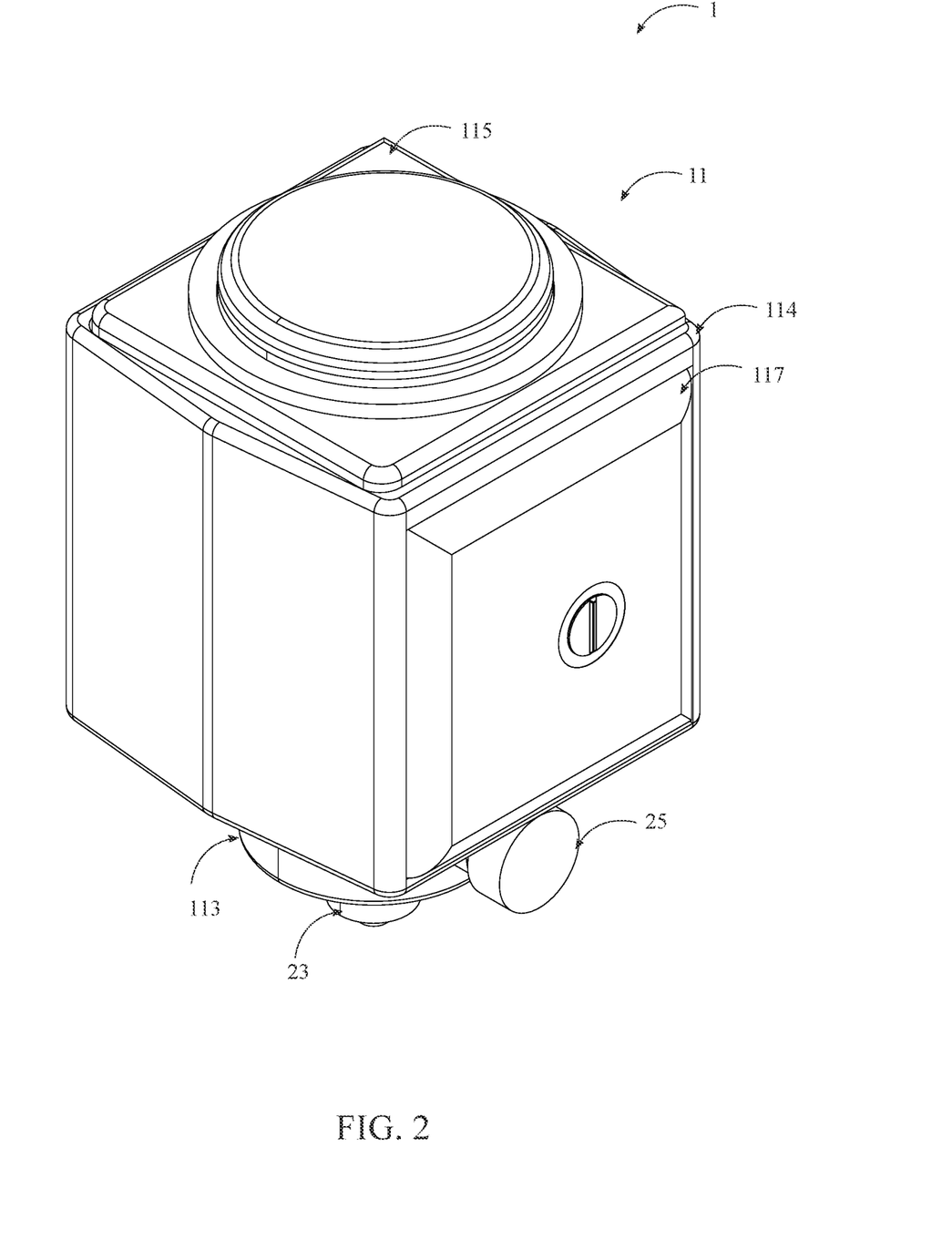
FIG. 2 is top perspective view of the present invention.
Figure 3:
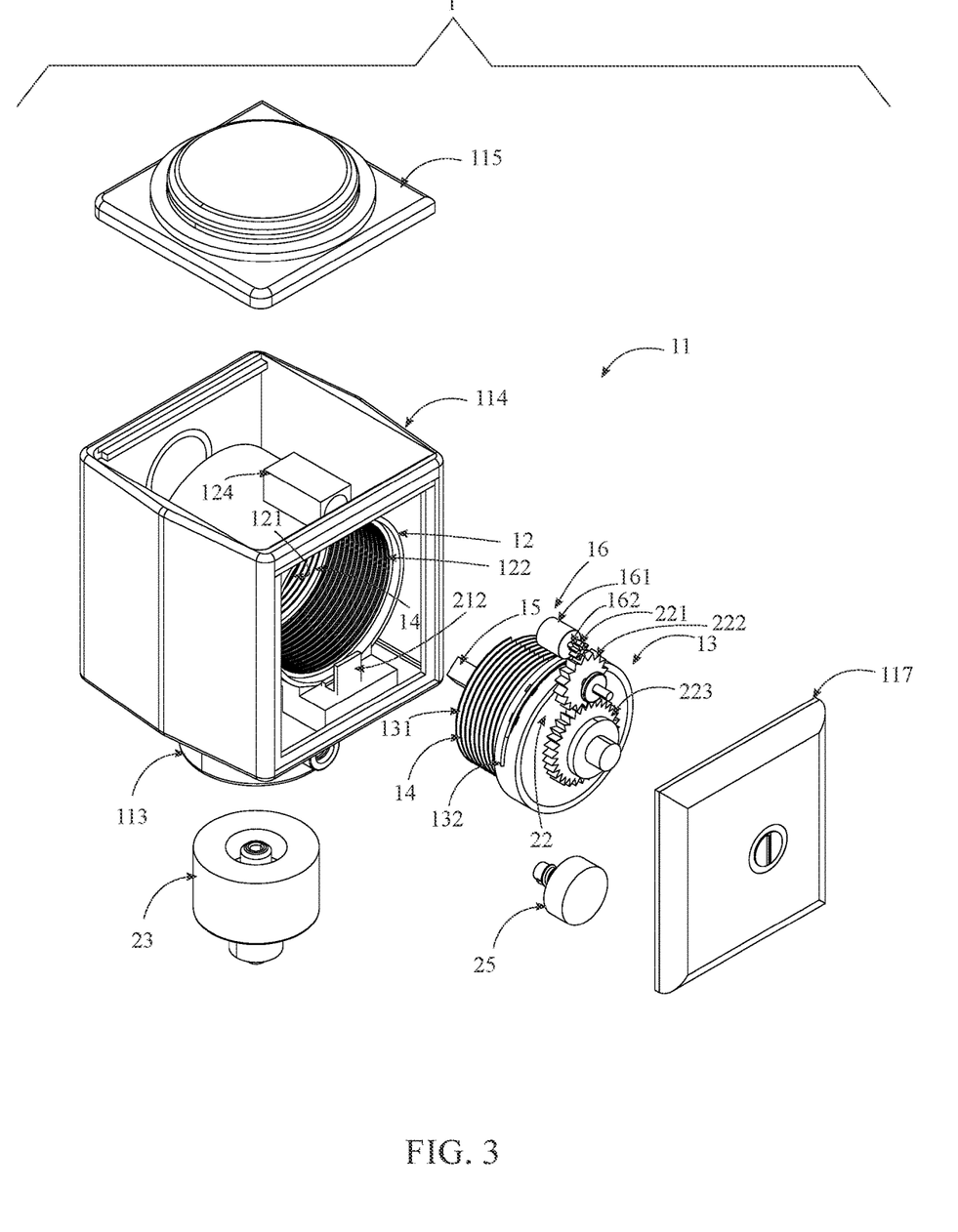
FIG. 3 is an exploded view of the present invention.
Figure 4:
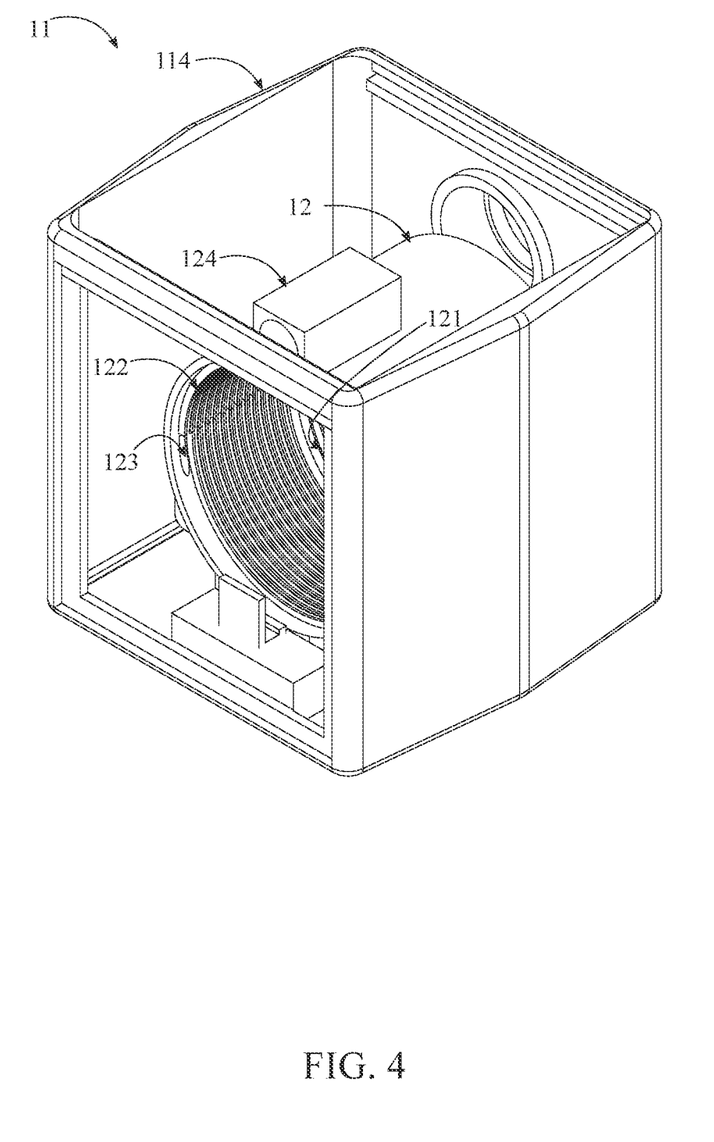
FIG. 4 is a perspective view of a reel housing used in the present invention.
Figure 5:
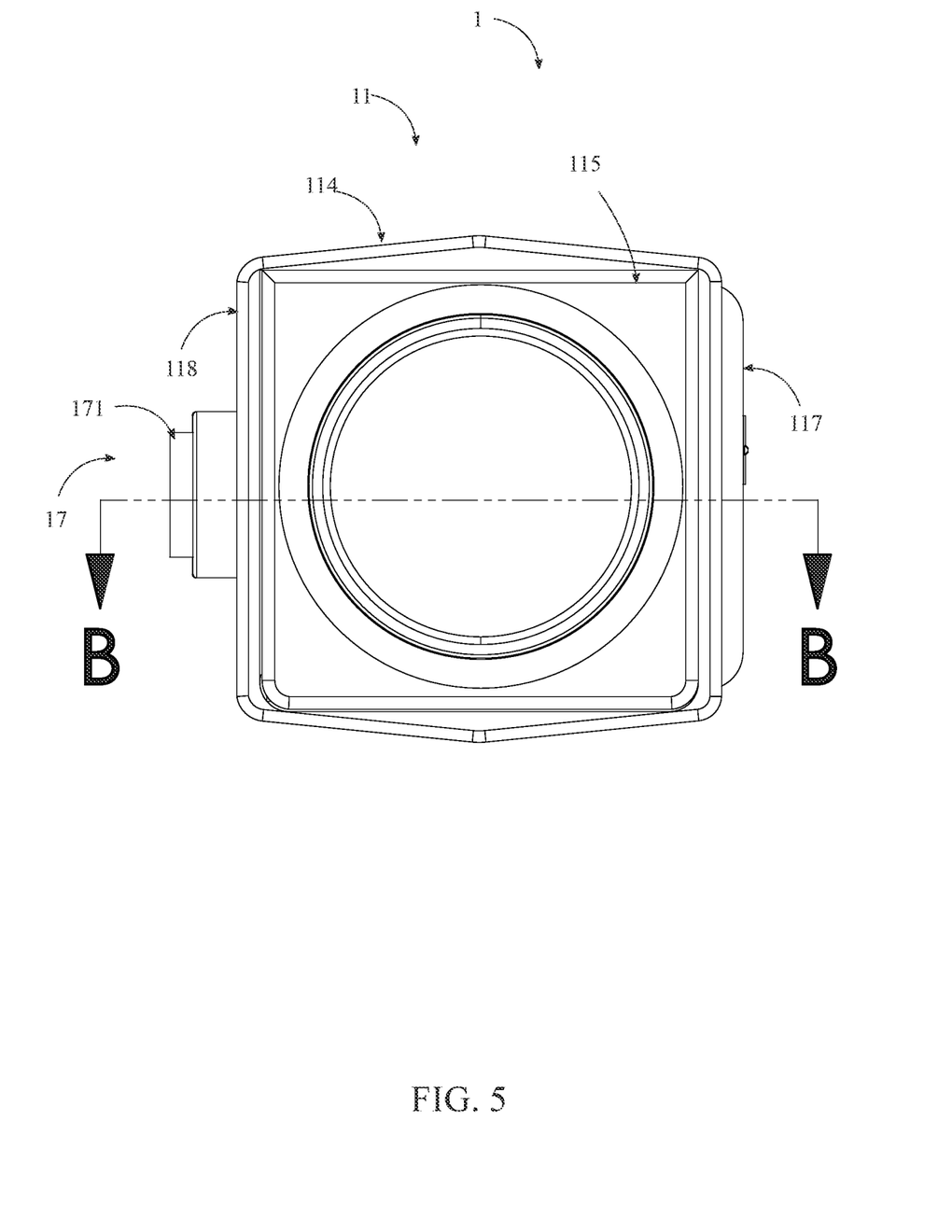
FIG. 5 is a top view of the present invention.

In reference to FIGS. 3-4, the spool drum 12 comprises a driver mount. The motor 16 comprises a stator and a rotor 162. The driver mount 124 is connected adjacent to the spool drum 12. The stator 161 is rotatably engaged to the rotor 162. The stator 161 is connected adjacent to the driver mount 124. In reference to FIG. 3, the motorized reel apparatus 1 further comprises a plurality of gears. In reference to FIG. 3, the plurality of gears 22 comprises a drive gear, a rotary gear 222, and a spindle gear 223. The drive gear 221 is torsionally connected to the rotor 162. The rotary gear 222 is rotatably connected adjacent to the reel housing 11. The spindle gear 223 is torsionally connected to the drive shaft 15. The rotary gear 222 is rotatably engaged between the drive gear 221 and the spindle gear 223. In the preferred embodiment, the driver mount 124 serves as a mounting implement to fix and mount the stator 161 portion of the motor 16 to the spool drum 12. In the preferred embodiment, the stator 161 takes the form of the static body of the motor. In the preferred embodiment, the rotor 162 takes the form of the rotary body of the motor 16 that mounts the drive gear 221. In the preferred embodiment, the plurality of gears 22 takes the form of any suitable gear system that transmits torque from the motor 16 to the drive shaft 15. In the preferred embodiment, the rotary gear 222 takes the form of the middle gear that bridges torque from the drive gear 221 to the spindle gear 223.

In reference to FIGS. 1-3 and 6, the motorized reel apparatus 1 further comprises a connection insert. In reference to FIGS. 1-3 and 6, the reel housing 11 further comprises a connection receiver. The connection receiver 113 is concentrically aligned to the wire outlet aperture 112. The connection insert 23 is connected along the connection receiver 113 through a fastening element 24. In reference to FIGS. 1-3 and 6, the motorized reel apparatus 1 further comprises a locking element. The locking element 25 is selectively engaged between the connection receiver 113 and the connection insert 23. In reference to FIGS. 1-6, the reel housing 11 further comprises a reel chassis, a top panel 115, and a base panel 116. The top panel 115 and the base panel 116 are terminally connected opposite to each other along the reel chassis 114. The reel housing 11 further comprises a side panel. The side panel 117 is connected adjacent to the reel chassis 114. The side panel 117 is connected between the top panel 115 and the base panel 116. The drive shaft 15 is rotatably connected to the side panel 117. The reel housing 11 further comprises an interface panel. The interface panel 118 is connected adjacent to the reel chassis 114, opposite to the side panel 117. The controller 17 is connected adjacent to the interface panel 118. In the preferred embodiment, the connection insert 23 takes the form of any suitable insert that facilitates the connection of a corresponding biopsy needle stylus. In the preferred embodiment, the connection receiver 113 serves as the main mounting body that mounts the connection insert 23 to the reel housing 11. In the preferred embodiment, the fastening element 24 takes the form of any suitable fastening element 24 that secures the connection insert 23 to the connection receiver 113. In the preferred embodiment, the fastening element 24 take the form of threaded connectors, but may take the form of any other suitable type of fastening implement. In the preferred embodiment, the locking element 25 takes the form of any suitable locking implement that secures the connection insert 23 to the connection receiver 113. Working in conjunction with the fastening element 24, the locking implement selectively engages the fastening element 24 to the connection receiver 113 such that the connection insert 23 does not unravel or unscrew from the connection receiver 113.

Although the invention has been explained in relation to its preferred embodiment, it is to be understood that many other possible modifications and variations can be made without departing from the spirit and scope of the invention as hereinafter claimed.

What is claimed is:

1. A motorized reel apparatus comprising:
   a reel housing;
   a spool drum;
   a spool spindle;
   an adjustment element;
   a drive shaft;
   a motor;
   a controller;
   the reel housing comprising a wire guide and a wire outlet aperture;
   the spool drum comprising a spindle receiving channel, a wire receiving groove, and a wire inlet;
   the spool spindle comprising a spindle body and a wire shuttle;
   the spool drum being connected within the reel housing;
   the spindle body being connected terminally adjacent to the wire shuttle;
   the spindle receiving channel traversing into the spool drum;
   the wire receiving groove traversing into the spool drum;
   the spindle body being operatively engaged to the spindle receiving channel through the adjustment element, wherein the spindle body is configured to rotate and traverse along the spool drum, and wherein the adjustment element is configured to adjust the spool spindle along the spool drum in length;
   the wire shuttle being operatively engaged to the wire receiving groove;
   the wire inlet traversing through the spool drum;
   the wire outlet aperture traversing through the reel housing;
   the wire guide being connected between the wire inlet and the wire outlet aperture;
   the wire shuttle, the wire inlet, and the wire guide being in fluid communication to each other;
   the drive shaft being rotatably connected within the reel housing;
   the drive shaft being torsionally engaged to the spool spindle;
   the drive shaft being slidably connected to the spool spindle;
   the drive shaft being rotatably engaged to the motor; and
   the controller being electrically connected to the motor.

2. The motorized reel apparatus as claimed in claim 1 comprising:
   a processing unit;
   an indicator unit;
   a plurality of sensors;
   a power supply;
   the processing unit comprising a power input terminal, a signal input terminal, a driver control module, and an indicator module;
   the power supply being electrically connected to the power input terminal;
   the plurality of sensors being electronically connected to the signal input terminal;
   the controller being electronically connected to the signal input terminal;
   the motor being electronically connected to the driver control module; and
   the indicator unit being electronically connected to the indicator control module.

3. The motorized reel apparatus as claimed in claim 2 comprising:
   the plurality of sensors comprising a first sensor and a second sensor;
   the first sensor being connected adjacent to the spool drum;
   the second sensor being connected adjacent to the spool drum, longitudinally opposite from the first sensor; and the first sensor and the second sensor being electronically connected to the signal input terminal.

4. The motorized reel apparatus as claimed in claim 3, wherein the first sensor and the second sensor are contact sensors.

5. The motorized reel apparatus as claimed in claim 2 comprising:
the indicator unit comprising a plurality of LED's;
the plurality of LED's being distributed within the reel housing; and
the plurality of LED's being electronically connected to the indicator control module.

6. The motorized reel apparatus as claimed in claim 2 comprising:
the controller comprising a first switch and a second switch;
the controller being connected adjacent to the reel housing;
the first switch and the second switch being distributed about the reel housing; and
the first switch and the second switch being electronically connected to the signal input terminal.

7. The motorized reel apparatus as claimed in claim 1 comprising:
the spool drum further comprising a driver mount;
the motor comprising a stator and a rotor;
the driver mount being connected adjacent to the spool drum;
the stator being rotatably engaged to the rotor; and
the stator being connected adjacent to the driver mount.

8. The motorized reel apparatus as claimed in claim 7 comprising:
a plurality of gears;
the plurality of gears comprising a drive gear, a rotary gear, and a spindle gear;
the drive gear being torsionally connected to the rotor;
the rotary gear being rotatably connected adjacent to the reel housing;
the spindle gear being torsionally connected to the drive shaft; and
the rotary gear being rotatably engaged between the drive gear and the spindle gear.

9. The motorized reel apparatus as claimed in claim 1 comprising:
a connection insert;
the reel housing further comprising a connection receiver;
the connection receiver being concentrically aligned to the wire outlet aperture; and
the connection insert being connected along the connection receiver through a fastening element.

10. The motorized reel apparatus as claimed in claim 9 comprising:
a locking element; and
the locking element being selectively engaged between the connection receiver and the connection insert.

11. The motorized reel apparatus as claimed in claim 1 comprising:
the reel housing further comprising a reel chassis, a top panel, and a base panel; and
the top panel and the base panel being terminally connected opposite to each other along the reel chassis.

12. The motorized reel apparatus as claimed in claim 11 comprising:
the reel housing further comprising a side panel;
the side panel being connected adjacent to the reel chassis;
the side panel being connected between the top panel and the base panel; and
the drive shaft being rotatably connected to the side panel.

13. The motorized reel apparatus as claimed in claim 12 comprising:
the reel housing further comprising an interface panel;
the interface panel being connected adjacent to the reel chassis, opposite to the side panel; and
the controller being connected adjacent to the interface panel.

* * * * *